US012805804B2

(12) United States Patent
Caparelli et al.

(10) Patent No.: US 12,805,804 B2
(45) Date of Patent: Nov. 24, 2026

(54) METHOD OF MANUFACTURING A FLEXIBLE SENSOR BELT AND A FLEXIBLE SENSOR BELT

(71) Applicant: Bambi Belt Holding B.V., S656 AE Eindhoven (NL)

(72) Inventors: Claudia Caparelli, Eindhoven (NL); Sidarto Bambang Oetomo, Waalre (NL); Chandan Manchikanti, Eindhoven (NL); Onorio Iervolino, Waalre (NL)

(73) Assignee: Bambi Belt Holding B.V., Eidenhoven (NL)

( * ) Notice: Subject to any disclaimer, the term of this patent is extended or adjusted under 35 U.S.C. 154(b) by 924 days.

(21) Appl. No.: 18/019,290

(22) PCT Filed: Aug. 3, 2021

(86) PCT No.: PCT/NL2021/050488

§ 371 (c)(1),
(2) Date: Jul. 24, 2023

(87) PCT Pub. No.: WO2022/031166

PCT Pub. Date: Feb. 10, 2022

(65) Prior Publication Data

US 2023/0270385 A1 Aug. 31, 2023

(30) Foreign Application Priority Data

Aug. 4, 2020 (NL) ..................................... 2026206

(51) Int. Cl.
*A61B 5/256* (2021.01)
*A61B 5/00* (2006.01)

(52) U.S. Cl.
CPC ............ *A61B 5/6831* (2013.01); *A61B 5/256* (2021.01); *A61B 5/6823* (2013.01);
(Continued)

(58) Field of Classification Search
CPC .............................. A61B 5/6831; B29C 45/00
See application file for complete search history.

(56) References Cited

U.S. PATENT DOCUMENTS 5,135,694 A * 8/1992 Akahane ........... B29C 45/14311
264/273
9,398,854 B2 * 7/2016 Proud .................. A61B 5/0024
(Continued)

FOREIGN PATENT DOCUMENTS

EP 3024535 6/2016
WO WO-1989/011386 11/1989
WO WO-2018/056811 3/2018

OTHER PUBLICATIONS

XP55783342 (Hamelmann Paul et al) Sensors; 19:5, Mar. 8, 2019, p. 1195.

(Continued)

*Primary Examiner* — Andrew D Graham
(74) *Attorney, Agent, or Firm* — Quarles & Brady LLP

(57) ABSTRACT

The present document relates to a method of manufacturing a flexible sensor belt suitable for being worn around an abdominal part of a human body, in particular a baby. The method comprising casting of a support layer using a flexible material in a first mould part, such that the support layer comprises one or more holes. Then, one or more electrodes are applied onto the support layer, such that these protrude the one or more holes. The electrodes are made of an electrically conductive material. The method further includes casting of a longitudinal belt section onto the support layer using a second mould part complementary to the first mould part, the casting applying the flexible material. The one or more electrodes are covered with the belt section formed on the support layer. The step of casting the
(Continued)

belt section comprises a step of retaining the one or more electrodes using one or more retaining elements.

10 Claims, 9 Drawing Sheets

(52) U.S. Cl.
CPC ..... *A61B 2503/045* (2013.01); *A61B 2505/03* (2013.01); *A61B 2562/0209* (2013.01); *A61B 2562/125* (2013.01); *A61B 2562/164* (2013.01); *A61B 2562/227* (2013.01)

(56) References Cited

U.S. PATENT DOCUMENTS

| | | | | |
|---|---|---|---|---|
| 9,526,422 | B2 * | 12/2016 | Proud | A61B 5/0024 |
| 2007/0161875 | A1 * | 7/2007 | Epley | A61B 5/11<br>600/595 |
| 2007/0231956 | A1 * | 10/2007 | Fukaya | H10W 74/016<br>438/106 |
| 2007/0246841 | A1 * | 10/2007 | Yamamoto | H10H 20/8506<br>257/784 |
| 2015/0230719 | A1 * | 8/2015 | Berg | A61B 5/6804<br>29/832 |
| 2015/0297145 | A1 * | 10/2015 | Luna | A61B 5/0205<br>600/509 |
| 2015/0359491 | A1 * | 12/2015 | Luna | A61B 5/0205<br>600/509 |
| 2016/0066841 | A1 * | 3/2016 | Cheng | A61B 5/681<br>600/390 |
| 2016/0066852 | A1 * | 3/2016 | Cheng | A61B 5/6831<br>600/390 |
| 2016/0066853 | A1 * | 3/2016 | Cheng | A61B 5/6831<br>600/390 |
| 2016/0073503 | A1 * | 3/2016 | Singleton | H05K 3/326<br>361/767 |
| 2016/0136882 | A1 * | 5/2016 | Cobbett | G16H 20/30<br>156/218 |
| 2016/0296141 | A1 * | 10/2016 | Rodiera Olivé | A61B 5/4519 |
| 2016/0367189 | A1 * | 12/2016 | Aimone | A61B 5/291 |
| 2017/0089782 | A1 * | 3/2017 | Hirt | A61B 5/681 |
| 2017/0209055 | A1 * | 7/2017 | Pantelopoulos | A61B 5/7203 |
| 2017/0271230 | A1 * | 9/2017 | Inaba | H10W 74/114 |
| 2017/0290530 | A1 * | 10/2017 | Hong | A61B 5/11 |
| 2017/0340237 | A1 | 11/2017 | Holzhacker et al. | |
| 2020/0015746 | A1 * | 1/2020 | Bambang Oetomo | A61B 5/0205 |

OTHER PUBLICATIONS

International Search Report, International Application No. PCT/NL2021/050488, mailed Feb. 3, 2022, 6 pages.

* cited by examiner

METHOD OF MANUFACTURING A FLEXIBLE SENSOR BELT AND A FLEXIBLE SENSOR BELT

CROSS REFERENCE TO RELATED APPLICATIONS

This application is a 35 U.S.C. § 371 national phase application of PCT/NL2021/050488 (WO-2022/031166-A2), filed on Aug. 3, 2021, entitled "MANUFACTURING A FLEXIBLE SENSOR BELT AND A FLEXIBLE SENSOR BELT", which claims the benefit of NL Patent Application No. 2026206, filed Aug. 4, 2020, each of which are incorporated herein by reference in their entirety.

FIELD OF INVENTION

The present invention is directed at a method of manufacturing a flexible sensor belt suitable for being worn around an abdominal part of a human body, in particular a baby, the method comprising the steps of: casting, using a first mould part, a support layer using a flexible material; and applying the one or more electrodes onto the support layer, wherein the electrodes are made of an electrically conductive material. The invention further relates to a flexible belt manufactured in this manner, as well as a mould part and a casting arrangement including mould parts.

BACKGROUND

The present document is particularly concerned with the manufacturing of medical aids for the nursing and caring of premature babies, i.e. babies having had a preterm birth. Preterm babies, i.e. babies that were born after a pregnancy of less than 37 weeks, are typically cared for by neonatal intensive care units (NICU) in hospitals, in isolation in an incubator while their vital signs are continuously monitored. Conventionally, such vital signs are monitored using conventional means for providing an electrocardiogram (ECG), such as to monitor their cardiac signal.

An ECG is commonly provided using adhesive electrodes adhered to the baby's body. Such electrodes are adhered to various parts of the body to detect different electrical physiological signals. Adhering of these electrodes is desired to ensure sufficient contact between the electrode and the skin, and to prevent accidental moving of the electrodes from their desired location on the body.

Although this method allows the baby's vital signs to be monitored in a reliable manner continuously, there are a number of disadvantages associated therewith. A main disadvantage is that the adhering of electrodes to the skin of the premature baby itself is not desired because the skin of preterm babies is very sensible. The use of adhesive electrodes is for that reason unpleasant and even harmful. Removal of the electrodes hurts the baby, causing stress to both the baby and his or her parents. Such removal occasionally may even damage the skin, causing small wounds and increasing the risk of infection. Taking into account that typically the electrodes are to be replaced every few days (e.g. every five days), it may be understood that this disadvantage is not negligible—in particular for babies that are to be monitored over a period of multiple weeks.

Recently, a new alternative manner for monitoring vital signs of a baby has been introduced in the form of a belt that can be worn around an abdominal part of a baby's body without the use of adhesives. This alternative is easy to apply, more comfortable to the baby and not harmful to the skin, while enabling reliable detection of the baby's vital signs for medical purposes and continuous monitoring. The belt is made of a polypropylene textile with a second layer of viscose fibers in order to absorb sweat. Electronics, connecting the sensing electrodes, are printed on a stretchable polyester substrate which is heat-bonded onto the viscose fibers. Furthermore, in addition to the cardiac signal, the proposed belt also enables to monitor the respiratory signal by enabling to provide an electromyogram (EMG) using the electrodes described.

Although the belt provides a highly advantageous alternative to the conventional methods of monitoring the vital signs of preterm babies, a disadvantage of the above construction is that the use of these different materials and their integration into the final belt is cumbersome during manufacturing and expensive. Furthermore, the belt is worn on the baby and attracts dirt, and therefore must be exchanged frequently. Textiles in particular attract and retain dirt. As may be appreciated, the belt described above is preferably a disposable product, and in view of these disadvantages the construction may become too expensive in use.

SUMMARY OF THE INVENTION

It is an object of the present invention to provide a method of manufacturing a flexible sensor belt, which overcomes the abovementioned disadvantages and provides an effective and low-cost manner of producing the flexible sensor belt.

To this end, in accordance with a first aspect of the invention, method of manufacturing a flexible sensor belt suitable for being worn around an abdominal part of a human body, in particular a baby, the method comprising the steps of: applying, one or more electrodes in a mould; casting, using the mould, a belt containing the electrodes by injecting a flexible material, such as to immerse the electrodes in the belt, and such that a contact area of the electrodes protrudes from the belt; wherein the step of casting the belt comprises a step of retaining the one or more electrodes using one or more retaining elements.

The casting takes place under high pressure and because of the lack of adhering, this may cause any other parts to move or deform. By retaining the electrodes, movement or destructive deformation thereof—which may be detrimental to a successful manufacturing process—is prevented. Therefore, after curing of the flexible material this method yields a flexible sensor belt with integrated electrodes, which are immersed in the flexible material.

In some embodiments, the method comprising the steps of: providing a support layer made of the flexible material; applying, onto the support layer, the one or more electrodes; and casting, a complementary layer onto the support layer using the flexible material, such as to cover the one or more electrodes with the complementary layer formed on the support layer to thereby immerse the electrodes in the flexible material.

In accordance with a preferred embodiment, there is provided a method of manufacturing a flexible sensor belt suitable for being worn around an abdominal part of a human body, in particular a baby, the method comprising the steps of: casting, using a first mould part, a support layer using a flexible material, such that the support layer comprises one or more holes; applying, onto the support layer, one or more electrodes, such that the one or more electrodes protrude the one or more holes, and wherein the electrodes are made of an electrically conductive material; casting, using a second mould part complementary to the first mould part, a longitudinal belt section onto the support layer using the flexible material, such as to cover the one or more electrodes with the belt section formed on the support layer to thereby immerse the electrodes in the flexible material; wherein the step of casting the belt section comprises a step of retaining the one or more electrodes using one or more retaining elements.

The manufacturing method described above yields a flexible sensor belt with integrated electrodes, which are fully immersed in the flexible material and thereby sealed from the exterior of the belt. Preferably, the material that is used is a liquid silicone rubber. Although these materials do not easily adhere to parts made of a different material, such as the electrodes or potentially any parts, by using the method of the invention the various parts may be retained in place during casting. The casting takes place under high pressure, and because of the lack of adhering, this may cause any other parts to move or deform. By retaining the electrodes, movement or destructive deformation thereof—which may be detrimental to a successful manufacturing process—is prevented. Therefore, after curing of the flexible material this method yields a flexible sensor belt with integrated electrodes, which are immersed in the flexible material. It is not essential that the support layer is the layer that comprises holes for the electrodes. Alternatively, the first layer may be the complementary layer, i.e. the longitudinal belt section. The electrodes are then retained on the complementary layer and the a further layer is injected immersing the electrodes (except the contact areas). Furthermore, the retaining may optionally be obtained by designing the electrodes or an electronic circuit with anchoring points (e.g. holes) and/or by the use of bonding agents.

The flexible sensor belt so produced is thus easy to manufacture, using a minimum of materials, and yields a low cost product that is therefore very suitable for disposable use. Also, the further advantage of a single piece sensor belt with integrated electronics that are immersed in the flexible material, is that dirt does not penetrate the material and may easily be removed. Therefore, the belt does not need to be replaced as frequent as conventional versions thereof. The belt is therefore more easy to use and it's use is less labor intensive. Any parts that are immersed in this way in the flexible material, are effectively sealed from the exterior, which therefore are protected and do not pose a threat to the child wearing the belt.

The advantages of the invention are already to some extend achieved in those embodiments wherein only the electrodes are embedded in the belt (between the support layer and the longitudinal belt part) and wiring for connecting the electrodes to a sensor module or other processing device is provided on a back side of the belt. However, in preferred embodiments the method further comprises a step of setting of the flexible material of belt section after casting thereof, wherein during said setting the method comprises retracting of the one or more retaining elements. In accordance with these embodiment, retracting of the retaining elements enables the—still liquid—flexible material to flow and fill up the spaces left by the retaining elements. Except for the parts protruding the holes of the support layer, the electrodes are thereafter sealed from the exterior of the belt.

The wiring, if present on an exterior part of the belt, may be connected to the electrodes and extend out of the flexible material to the exterior of the belt. The electrical conductive paths to a processing device or sensor module may, in accordance with some of these embodiments of the flexible sensor belt, be provided by an electronic circuit embedded in the belt. In these cases, in the method of the invention, in accordance with some embodiments, the step of applying the one or more electrodes comprises applying a flexible electronic circuit such as to electrically connect the one or one or electrodes to the support layer. This may be achieved in various ways. In some embodiments, the electronic circuit is attached to the one or more electrodes after applying the electrodes onto the support layer. A conductive glue or silicone adhesive may be used to apply glue layer to adhere the electrodes to the electronic circuit, e.g. to prevent elevated temperatures required for soldering. The glue for example may be a cyanoacrylate or a two-part conductive epoxy, although the skilled person will recognize suitable alternatives for the glue. In some other embodiments, another way to apply the electronic circuit may be, to attach the electronic circuit to the one or more electrodes, and thereafter to apply the electronic circuit including the electrodes onto the support layer. In these embodiments, as an alternative to the application of glue (which also in these embodiments is a possible implementation), it is also possible to perform soldering in order to attach the electrodes to the circuit. As a further alternative embodiment, the electronic circuit and the one or more electrodes may be integrally formed, and the integrally formed circuit is applied to the support layer. This prevents the need for bonding by soldering or gluing, as the electrodes and the circuit form an integral part.

In some embodiments, the flexible electronic circuit comprises one or more conductive paths, the one or more conductive paths being shaped such as to form at least one of: a wavy path; a zigzag path; or a meandering path. In some of these embodiments, the method may comprise, during said casting of the belt section, a step of retaining the one or more conductive paths using one or more retaining elements. Here retaining elements are applied to retain the conductive paths in place, which may otherwise tend to bend, curl or displace during casting.

The present invention, in accordance with a second aspect thereof, provides a flexible sensor belt manufactured using a method according to the first aspect, wherein the sensor belt is suitable for being worn around an abdominal part of a human body, in particular a baby, the sensor belt comprising a support layer made of a flexible material including one or more holes, one or more electrodes made of a conductive material and protruding through the one or more holes such as to be in contact with a skin of the body in use, and a longitudinal belt section covering the one or more electrodes on the support layer, wherein the electrodes are immersed in the flexible material between the support layer and the longitudinal belt section. The flexible material preferably comprises a liquid silicone rubber, but may alternatively or additionally comprise at least one of: a thermoplastic elastomer, latex.

The present invention, in accordance with a third aspect thereof, provides a mould part for use as a second mould part complementary to a first mould part in a method according to the first aspect, the first and second mould parts being comprised by a casting assembly, wherein the mould part comprises a recess which in use cooperates with a complementary recess in the first mould part such as to form an internal space, wherein the internal space is suitably shaped to enable forming a longitudinal belt section by means of casting of a flexible material, such that the longitudinal belt section is thereby formed onto a support layer in the complementary recess of the first mould part for covering one or more electrodes on the support layer, wherein the mould part is configured for providing one or more retaining elements in the internal space such as to retain the one or more electrodes in place during casting of the flexible material, for covering the one or more electrodes with the belt section formed on the support layer to thereby immerse the electrodes in the flexible material.

In some embodiments, the mould part comprises one or more through holes or slots for receiving the one or more retaining elements therethrough such as to retain the one or more electrodes in place during casting of the flexible material. The benefits thereof are that the one or more retaining elements may be extended through the holes to retain the electrodes or the conductive path of a circuit, whereas during casting they may optionally be retracted via the holes. Also, retractable retaining elements may be mounted in the holes, from which they may be extended into the internal space. Hence, in some embodiments, the mould part itself comprises the one or more retaining elements, the one or more retaining elements extending in or are extendable into the internal space. In other embodiments, these may be external to the mould and extended therein via the holes.

In some embodiments, the mould part is configured for providing the one or more retaining elements in at least one of: one or more positions opposite an area or circumference of an area corresponding with a location of one or more holes in a support layer to be formed in the first mould part; or one or more positions corresponding with a location of a conductive path of an electronic circuit interconnecting the one or more electrodes. The abovementioned positions correspond with positions of the elements to be retained, such as the electrodes or the circuit paths. Of course, the retaining elements may additionally or alternatively be present in other parts of mould.

The invention, in accordance with a fourth aspect thereof, provides a casting assembly comprising a mould part in accordance with the third aspect for use as a second mould part in a method according to the first aspect of the invention. The casting assembly further includes a first mould part for use in said method, wherein the casting assembly further includes a third mould part for applying one or more electrodes to a support layer formed in the first mould part, and such that the electrodes protrude one or more holes in the support layer.

BRIEF DESCRIPTION OF THE DRAWINGS

The invention will further be elucidated by description of some specific embodiments thereof, making reference to the attached drawings. The detailed description provides examples of possible implementations of the invention, but is not to be regarded as describing the only embodiments falling under the scope. The scope of the invention is defined in the claims, and the description is to be regarded as illustrative without being restrictive on the invention. In the drawings:

DETAILED DESCRIPTION

Figure 1:
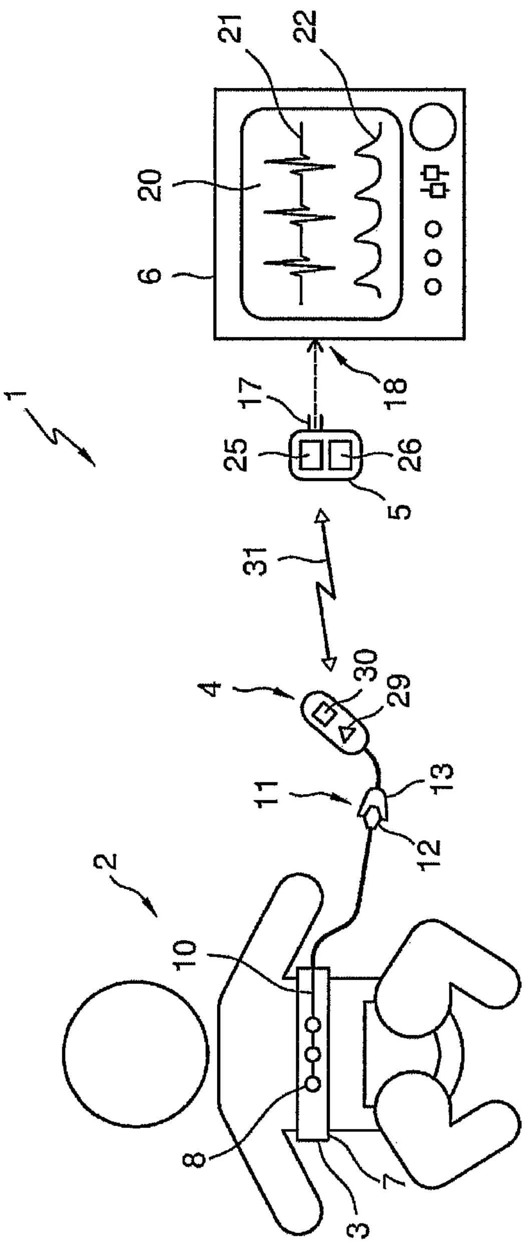
FIG. 1 schematically illustrates a system in accordance with an embodiment of the present invention.

FIG. 1 schematically illustrates a system 1 in in accordance with an embodiment of the present invention. The system 1 comprises a wearable device 7, embodied as a belt 3 to be worn around an abdominal part of the body 2 of a preterm baby. It is not essential that the wearable device 7 is embodied as a belt 3, and in principle the wearable device 7 may be embodied differently, for example as a harness. The wearable device in accordance with the invention includes or provides a carrier, here the belt 3, to the electrodes and other components. Hereafter, it will be assumed that the wearable device 7 is embodied as a belt 3, and that the belt 3 itself is the carrier. Therefore, the terms 'carrier' and 'belt' may sometimes have been interchanged in the text, and be referred to by the same reference numeral.

The belt 3 comprises a plurality of electrodes 8 that make contact with the skin of the baby 2. The electrodes 8 receive electric physiological signals from the body 2 of the baby, in particular from the muscles from which the respiratory signal may be obtained, and from the heart of the baby 2. The belt 3 is connected to a sensor unit 4 which receives the electric physiological signals from the electrodes 8, and amplifies these using amplifier circuitry 29. The sensor unit 4, from the signals received from the electrodes 8, generates a sensor signal. The sensor signal is transmitted to a receiver unit 5, which processes the signal, and provided to a monitor unit 6 for presentation on a display 20.

The sensor signals from the sensor unit 4 will be transmitted wirelessly, via wireless signal 31, to the receiver unit 5. To this end, the sensor unit 4 comprises a data communication unit 30. Similarly, the receiver unit 5 likewise comprises a data communication unit 26. For example, the communication units 30 and 26, may be configured for enabling data communication via Bluetooth low energy, however, alternative data communication protocols may likewise be applied by the units 26 and 30. The receiver unit 5 further comprises a processor 25 that is configured for processing the sensor signals and provide vital signs signals to the monitor 6. The processor may apply certain algorithms that are stored in a memory of the receiver module 5 to perform this task.

The receiver unit 5 is connected to that monitor 6 using a third connector 17 which is received in a cradle or fourth connector 18 in the monitor unit 6. As mentioned herein before, Dependent on the embodiment, the receiver unit 5 may be connected in a different way to the monitor 6. For example, the receiver unit 5 may have a wired connection and a plug that connects to a socket in the monitor 6. The receiver unit 5 may alternatively apply wireless communication to the monitor 6 in yet a different embodiment, without departing from the present invention. Also, in a preferred embodiment, receiver unit 5 may be integrated into the monitor 6 via the cradle 18.

The monitor 6 comprises a display 20 in which the vital sign signals our present it two, for example, the medical staff. For example, the monitor unit 6 may present a heart rate signal 20 and a respiratory signal 21.

The connection between the belt 3 and the sensor unit 4 is provided via a connector assembly 11. The connector assembly 11 consists of eight first connector 12 and a second connector 13 that are complementary to each other, in the sense that they are cooperatively shaped to enable a tight mechanical and electrical connection. The electric physiological signals from the electrodes 8 are provided to the first connector 12 via a conductive path 10. The conductive path 10 is provided by an electric circuit 40 (not shown) That is sufficiently flexible for the flexible belt 3.

Figure 2:
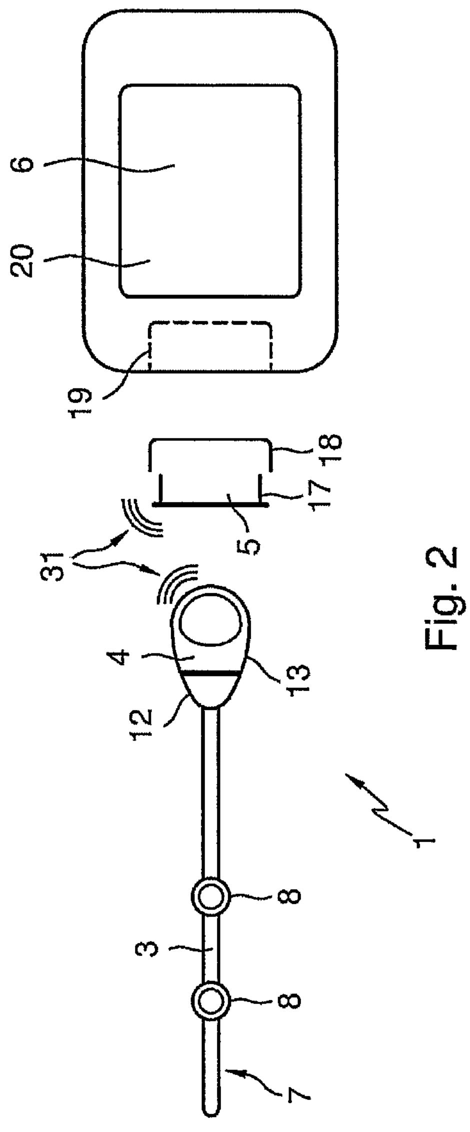
FIG. 2 schematically illustrates a system in accordance with an embodiment of the present invention.

FIG. 2 provides a further schematic of the system 1 in accordance with an embodiment of the present invention. The elements in FIG. 2 that correspond with the elements in FIG. 1 are designated by means of corresponding reference signs. In addition to these, FIG. 2 schematically illustrates the internal space 19 in the monitor 6 wherein the cradle 18 or fourth connector 18 maybe mounted.

Figure 3:
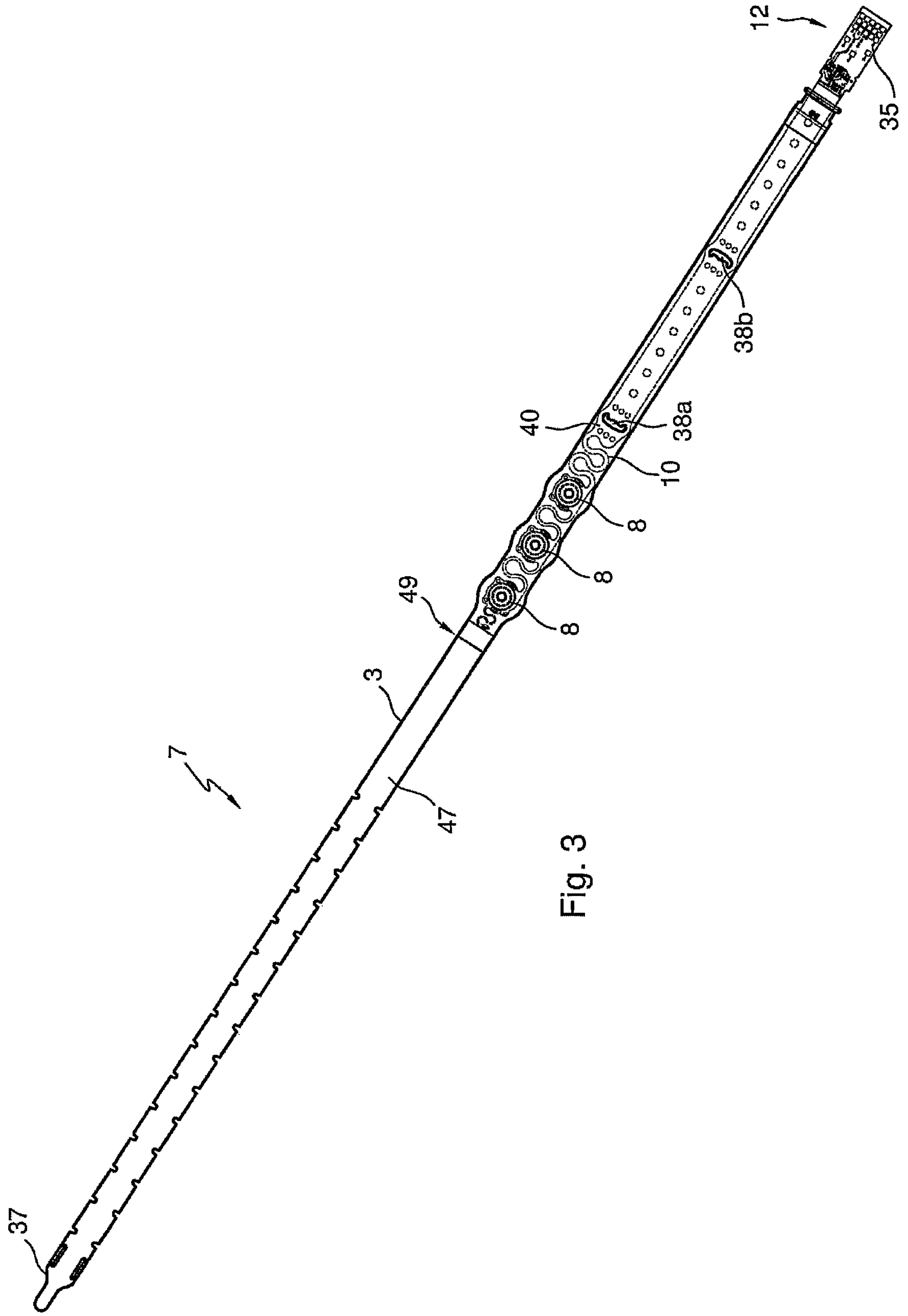
FIG. 3 illustrates a wearable device in accordance with an embodiment of the present invention.

FIG. 3 provides an illustration of the belt 3, forming the wearable device 7, for use in a system 1 in accordance with an embodiment of the present invention. The belt 3 comprises the electrodes 8 and a flexible electronics circuit 40 that provides the conductive paths 10. The flexible electronic circuit 40 extends over the length of the belt 3 into the first connector 12. Internally, the first connector 12 comprises an electronic circuit 35. The conductive path 10 of the electronic circuit 40 are connected to the circuit 35 of the first connector 12, enabling to establish an electrically conductive connection with the sensor unit 4 or a receiver unit 5 which comprise a second connector 13 in order to form a connector assembly 11. The external part of the first connector 12 comprises a housing 45 (see FIG. 4B) that is correspondingly shaped such as to be complementary to the second connector 13. The complementary shapes provide a robust mechanical connection enabling the establishing of a functional electrical connection in order to bear the electric physiological signals. Furthermore, the belt 3 on its other ultimate end 37 comprises means that cooperate with openings 38*a* and 38*b* to enable wearing of the belt 3 around the abdominal parts of the body 2 of the baby.

Figure 4A:
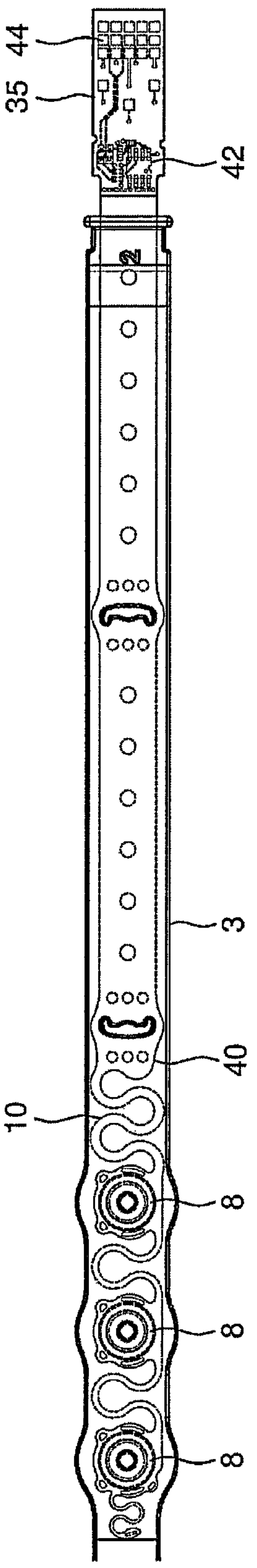
FIG. 4A is an enlargement of a part of the wearable device illustrated in FIG. 3.

FIG. 4A is an enlargement of the belt 3 that is depicted in FIG. 3. The figure more clearly illustrates the flexible electronic circuit 40 providing the conductive paths 10. The conductive paths 10 are shaped such as to meander between the lateral sides of the belt 3, and thereby provide flexibility in the longitudinal direction of the belt 3 to the electronic circuit 40. This enables stretching of the belt without breaking the circuit 40. Alternatively, a wavy or zigzag path also provides such flexibility. The belt 3 itself may be fabricated from a liquid silicone rubber, which is flexible and can be easily cleaned. FIG. 4A further illustrates the internal circuit 35 of the first connector 12. Electrical connections are provided via the conductive pads 44 on the circuit 35, and are contact by cooperating conductive elements in the second connector 13 of the sensor unit 4. A memory chip 42 may be optionally present for storing data, such as the identification key data for enabling secure data communication between the sensor unit 4 and the receiver unit 5, as will be explained later. Once assembled, the circuit 35 will reside inside the housing 45 of the first connector 12 illustrated in FIG. 4B.

Figure 4C:
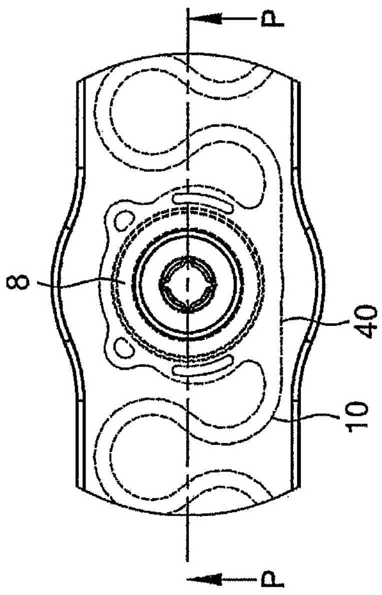
FIG. 4C Illustrates an enlarged part of the wearable device FIG. 3.
Figure 4B:
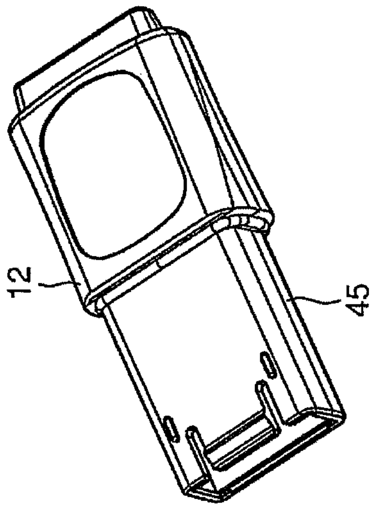
FIG. 4B illustrates a first connector in accordance with an embodiment of the invention.
Figure 4D:
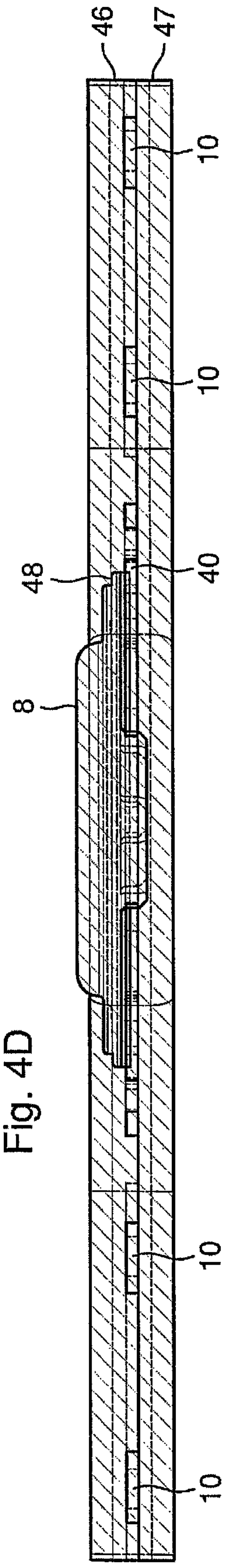
FIG. 4D illustrates a cross section of the enlargement of FIG. 4C.

Furthermore a close-up of an electrode 8 and the circuitry around the electrode 8 is illustrated in FIG. 4C. The figure shows the circuitry 40 and the meandering conductive path 10. A cross section across the line P-P is illustrated in FIG. 4D. The belt 3 consists of an upper layer, or support layer 46 and a lower layer forming a longitudinal belt section 47. The longitudinal belt section 47 extends from end to end on the belt 3, as is depicted in FIG. 3, all the way towards the ultimate end 37. The support layer 46 only extends over a part of the length of the belt 3, until the demarcation 49 illustrated in FIG. 3. FIG. 4D, in cross section illustrates how the electrode 8 protrudes through an opening in the support layer 46 of the belt 3 in order to enable making contact with the skin of the body 2 of the baby. It is clear from FIG. 4D that circuitry 40 is encapsulated inside the material of the belt 3, between the support layer 46 and the longitudinal belt section 47. The belt 3 is manufactured by molding the support layer 46 of the belt 3 first, and thereafter mounting the electrodes 8 in the openings 78 (FIG. 9) and applying the circuitry 40. Then, the longitudinal belt section 47 of the belt 3 is molded onto the support layer 46 in order to encapsulate the backsides of the electrodes 8 and the circuitry 40 inside the belt 3. Layer 48 is an adhesive layer, comprising a conductive adhesive, that allows to connect the electrodes 8 to the circuitry 40. A conductive glue may be used in layer 48 to adhere the electrodes 8 to the electronic circuit 40. The glue in layer 48 for example may be a cyanoacrylate or a two-part conductive epoxy, although the skilled person will recognize suitable alternatives.

Another way to apply the electronic circuit 40 to the electrodes 8, in accordance with some other embodiments, may be, to attach the electronic circuit 40 to the one or more electrodes 8, and thereafter to apply the electronic circuit 40 including the electrodes 8 onto the upper layer of the belt 3. In these embodiments, as an alternative to the application of glue, it may also be possible to perform soldering. Furthermore, in yet an alternative embodiment, the electronic circuit 40 and the electrodes 8 may be integrally formed as one element. The integrally formed circuit 40 with electrodes 8 and conductive paths 10 may then be applied to the upper layer of the belt 3 at once.

Furthermore, during casting of the longitudinal belt section 47 onto the support layer 46, the electrodes 8 and optionally, but preferably, the meandering conductive paths 10, are held in place by retaining elements. The flexible material will, during moulding, be injected into the second mould part 72 under high pressure. Without maintaining the electrodes and the conductive paths 10 in place, they may be displaced or deformed during the moulding. The manufacturing process will be described further down below.

Figure 5A:
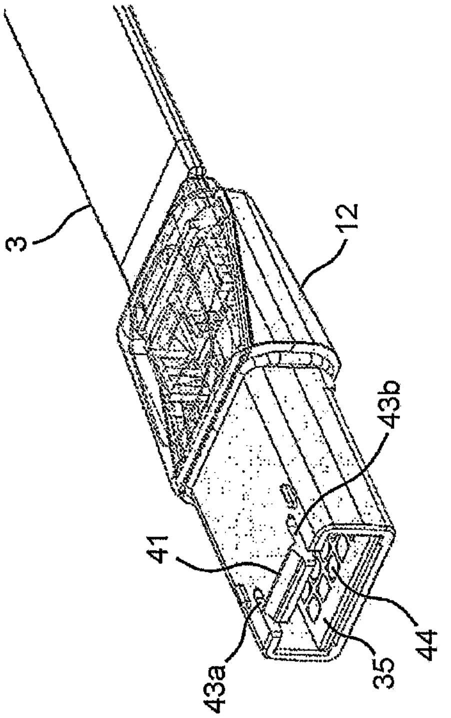
FIG. 5A Illustrates a first connector in accordance with an embodiment of the invention.
Figure 5B:
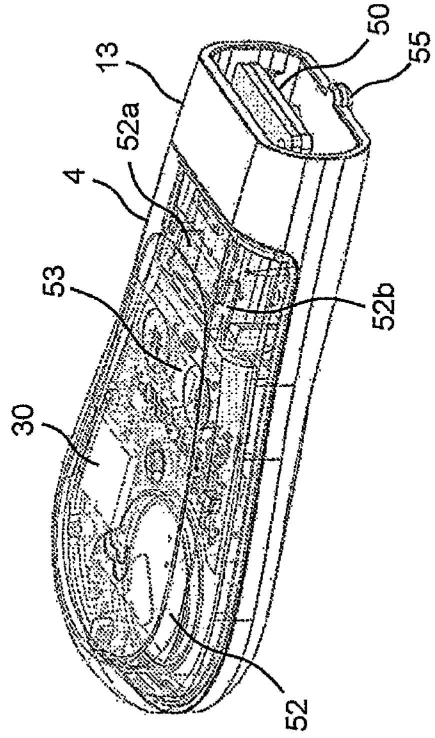
FIG. 5B illustrates a sensor unit in accordance with an embodiment of the invention.
Figure 5C:
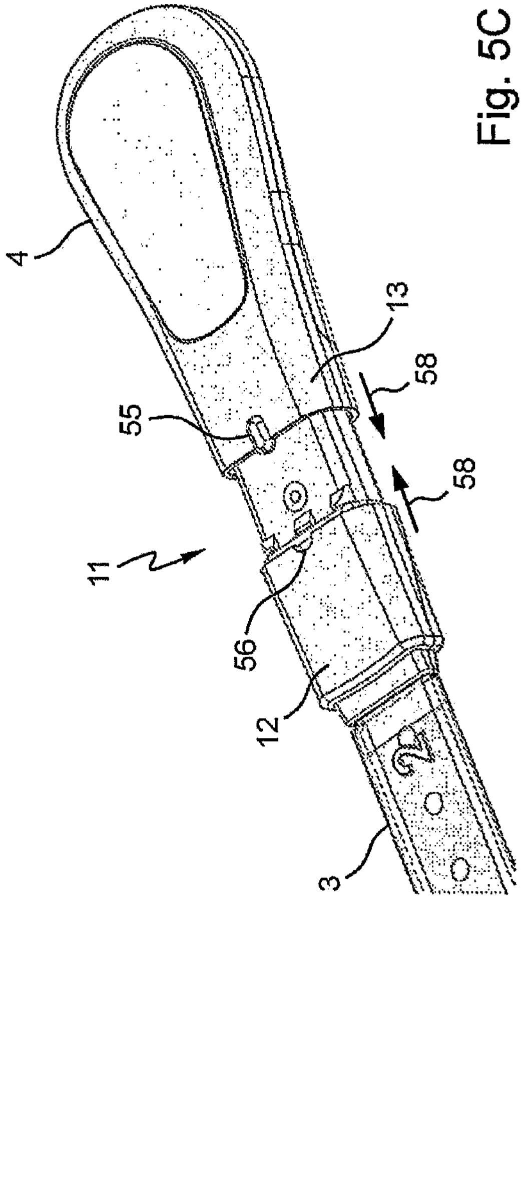
FIG. 5C illustrates a connector assembly in accordance with an embodiment of the present invention.

FIGS. 5A, 5B and 5C respectively illustrate the first connector 12, the sensor unit 4, and a connector assembly 11. In FIG. 5A, the first connector 12 in its assembled form can be seen including the internal circuit 35 bearing the memory chip 42 (not shown, but visible in FIG. 4A). The first connector 12 comprises a snapper 41 that corresponds with a ditch (not visible) inside the second connector 13, providing mechanical stability and a tactile feedback to the user that the connection has been correctly made. Furthermore, the connectors 12 and 13 may be designed such that they may only be connected in one way. For that reason, the first connector 12 comprises two slits 43*a* and 43*b* in the top. Slits of this kind are also needed to form the snapper 41. The second connector 13 correspondingly has two ribs 52*a* and 52*b* that fall into the slits 43*a* and 43*b* upon connection thereof.

FIG. 5B illustrates the sensor unit 4 including the second connector 13. A complementary element 50, which is complementary to the circuit 35 in order to establish electrical connections, extends towards the opening of the second connector 13. FIG. 5B also illustrates the data communication unit 30 and a battery 52. The electronic components 53 form the amplifier 29 illustrated in FIG. 1 to amplify the electric physiological signals from the electrodes 8. Furthermore, on a bottom side of the second connector 13 there is a small ridge 55 that, in use, extents over the first connector 12.

As can be seen in FIG. 5C, the first connector 12 likewise has a small indentation 56 that corresponds with the ridge 55. This indicates to a user the orientation of how to connect the two parts 12 and 13. The connection is made by inserting the first connector 12 into the second connector 13 in the way indicated by the arrows 58 to establish the connector assembly 11. The use of the connector assembly in the system 1 is advantageous in order to obtain a flexible and low-cost solution that allows to provide a disposable wearable device 7 in combination with good quality or even high end sensor unit 4. Furthermore, the connector assembly 11 makes it possible to exchange the wearable device 7 and sensor units 4 each within their own maintenance cycle, such as to enable different maintenance cycles for replacing the belt 3 for hygienic reasons and changing the sensor unit 4 in order to charge the battery 52.

Figure 6B:
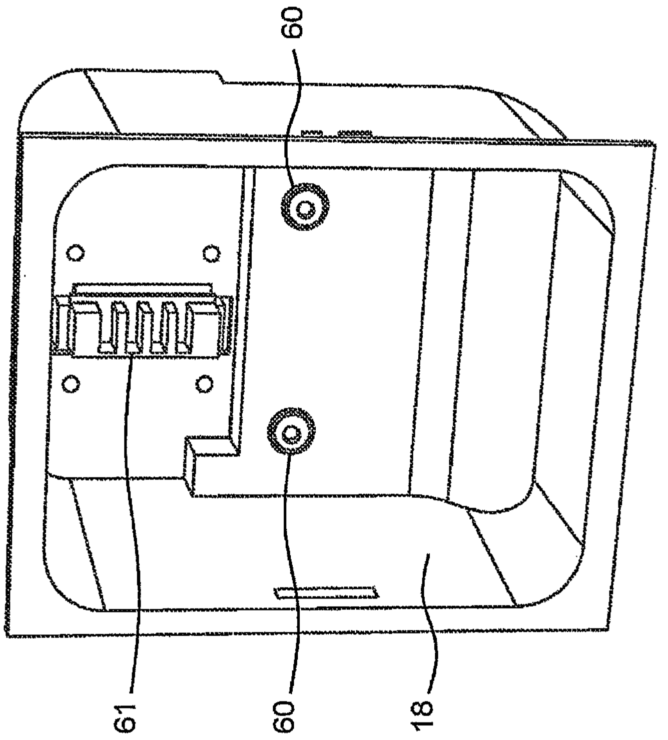
FIG. 6B illustrates a cradle or third connector in accordance with an embodiment of the present invention.
Figure 6A:
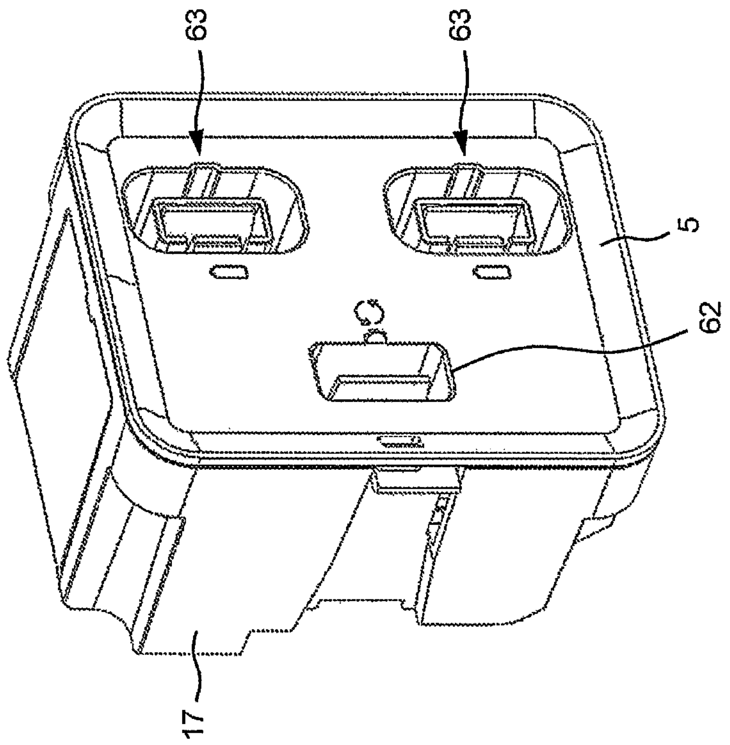
FIG. 6A Illustrates a receiver unit in accordance with an embodiment of the present invention.

A further synergy is obtained by enabling the receiver unit 5 to be connected directly to the belt 3. To this end, as illustrated in FIG. 6A, the receiver unit 5 includes a further second connector 62 which allows to make such a connection. Again, the ridge 66 on the periphery of the further second connector 62 provides an indication of how to connect the first connector 12 of the belt 3 with the further second connector 62 of the receiver unit. As mentioned above, the receiver unit 5 may comprise a processor 25, which inter alia, may be configured to generate identification key data associated with unique identification keys. For example, unique identification keys may be assembled by combining an exact time of generating the key with a serial number of the receiver module and/or a serial number of the wearable device 7 that will receive the key. However, there are numerous ways in which a unique identification key may be assembled, e.g. by using prime numbers or by other combinations of data and time or location stamps. The skilled person will recognize the various ways in which this may be implemented. The further second connector 62 may well be used advantageously to connect a belt 3 to the receiver unit 5 in order to exchange data, such as the generated identification key data. In addition to the further second connector 62, the receiver unit 5 may comprise one or more fifth connectors 63 that enable to physically connect sensor units 4 to the receiver unit 5. This, for example, enables charging of the batteries 52 of the sensor modules 4.

The receiver unit 5 may be connected to the monitor 6 using an adapter or cradle 18. The cradle 18 may be mounted to a monitor unit 6 that is dedicated for use with the receiver unit 5, and allows to mount the cradle 18. The cradle 18 is fixed to the monitor by mounting screws 60, and a data exchange port 61 enables connection to a corresponding port on the receiver unit 5. The cradle 18 is designed to receive the backside 17 of the receiver unit 5, forming a third connector 17 and a fourth connector 18. Instead of the cradle 18 applied in this embodiment, it is of course also possible to use smaller connectors or a simple plug and socket type connection to exchange data signals, such as the vital sign signals.

By enabling the receiver unit 5 to be connected to the belt 3 via the first connector 12, it becomes possible to store the identification key date in a secure manner into the memory chip 42 of the belt 3. This can be used in various ways to increase the safety of use of the disposable belts 3 using a pairing method in order to associate the respective belt 3 with the receiver module. For example, the identification key data can be obtained by the sensor unit 4 in order to enable secure data communication between the communications units 30 and 26 of the sensor unit 4 and the receiver unit 5 respectively. Hereto, the unique identification key can be used to encrypt or encode the data, or to signal to the receiver unit 5 that the sensor signal that is wirelessly transmitted is indeed coming from the correct sensor unit 4. Furthermore, the presence of identification key data 115 (see FIG. 11) in the memory 42 of the belt 3, may indicate to the receiver module 5 that the belt 3 has already been used before, enabling the receiver unit 5 to trigger an alarm or a red warning light. Similarly, the absence of an identification key data in the memory may indicate that the belt 3 is a new and clean or sterile belt, enabling the receiver unit 5 to trigger a green light. As may be appreciated the colors of the suggested warning lights are purely at the choice of the skilled person, without deviating from the invention.

Figure 11:
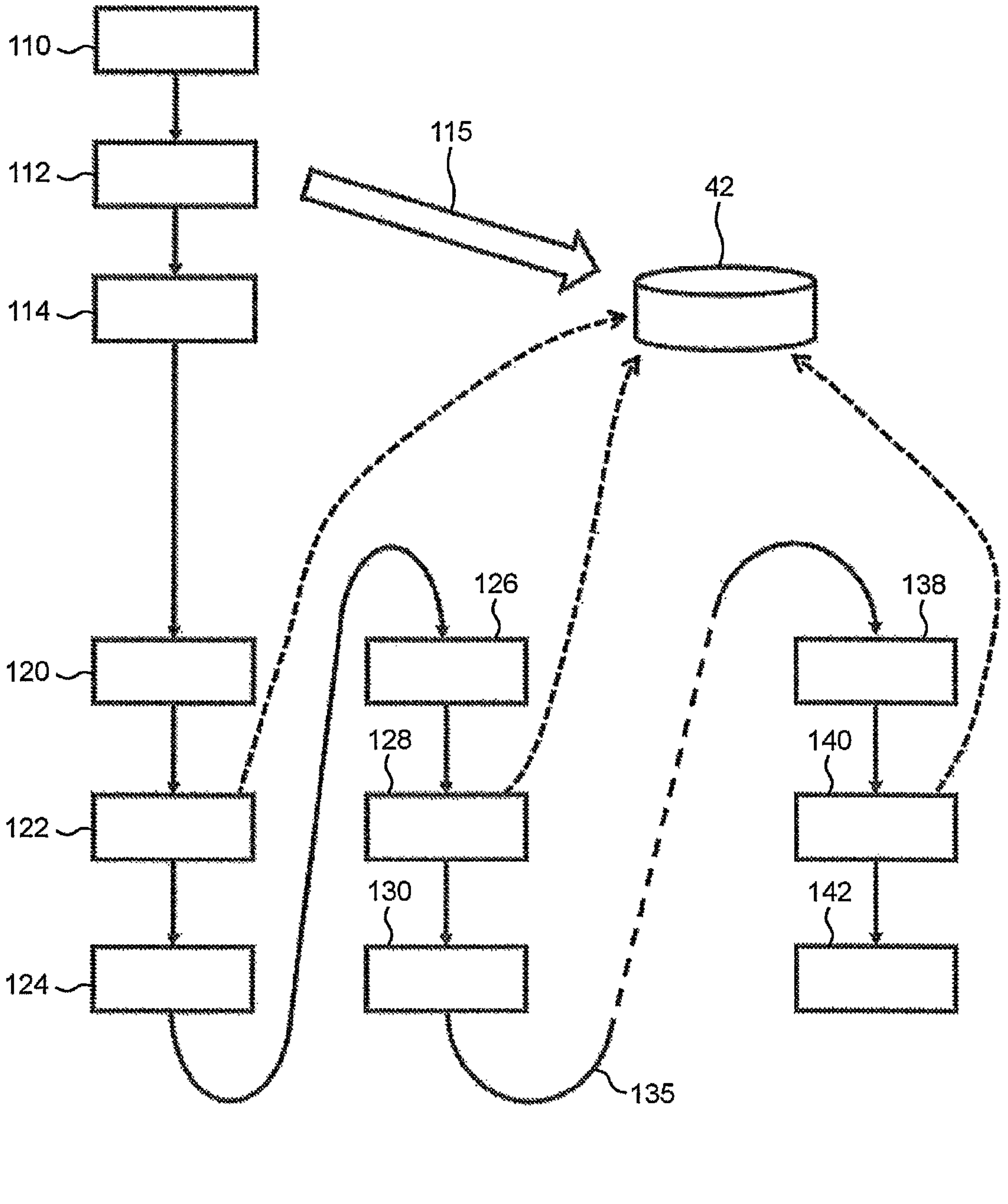
FIG. 11 schematically illustrates a pairing method that can be used in a system in accordance with the present invention.

FIG. 11 schematically illustrates a pairing method in accordance with an embodiment of the present invention. The method starts in step 110 by connecting the first connector 12 to the further second connector 62 of the receiver unit 5. Then, in step 112, the identification key data 115 generated by processor 25 of the receiver unit 5 is transmitted to the memory 42 in the first connector and stored therein. Optionally, a check may be carried out first to verify if the memory 42 of belt 3 already contains an identification key data 115, which would indicate that the belt is already used. This may cause the receiver unit 5 to trigger an alarm signal (sound, light, vibration, spoken voice, etc.). If the identification key data 115 has been stored, then in step 114 the first connector 12 will be disconnected from the receiver unit 5. The receiver unit 5 and the belt 3 are now paired, and both units 5 and 3 will contain the identification key data 115 in their respective memories. Typically, this is performed prior to putting the belt 3 on the baby 2.

Next, a sensor unit 4—which may be any arbitrary sensor unit—will be connected to the belt 3 in step 120, and in step 122 the identification key data 115 will be retrieved by the sensor unit 4 from the memory 42 in the belt 3. The belt 3 and the connected sensor unit 4 are now operational to obtain the electric physiological signals from the electrodes 8 and provide a sensor signal wirelessly to the receiver unit 5, where it is processed by the processor 25 and presented via the monitor 6. After a while, when the battery 52 of the sensor unit 4 becomes drained, the sensor unit 4 is disconnected in step 124 and connected to one of the ports 63 of the receiver unit 5 for charging. Directly upon disconnecting in step 124, a new sensor unit 4 will be connected in step 126 and in step 128 the identification key data 115 will be retrieved by the sensor unit 4 from the memory 42 in the belt 3. Again, when the battery 52 of this second sensor unit 4 becomes drained, the sensor unit 4 is disconnected in step 130 and connected to one of the ports 63 of the receiver unit

5 for charging. A further sensor unit may then be connected (e.g. the first sensor unit which has been charged in the meantime) and so on. In FIG. 11, this has been illustrated by the further steps 138, 140 and 142, which correspond to the steps of connecting (step 138), retrieving the identification data (step 140), and disconnecting the unit when charging is needed. The half dotted line 135 indicates that any number of sensor units 4 can be connected in this way until the belt 3 needs to be replaced. The pairing is performed between the receiver unit 5 and the belt 3, and by storing the identification key data in the memory 42 of the belt, any arbitrary sensor unit 4 can be used with belt 3. The pairing ensures that the monitor 6 only shows the vital sign signals from the belt with which the receiver unit 5 is paired, and not from any other belt in the vicinity. This is a safety measure.

Figure 7:
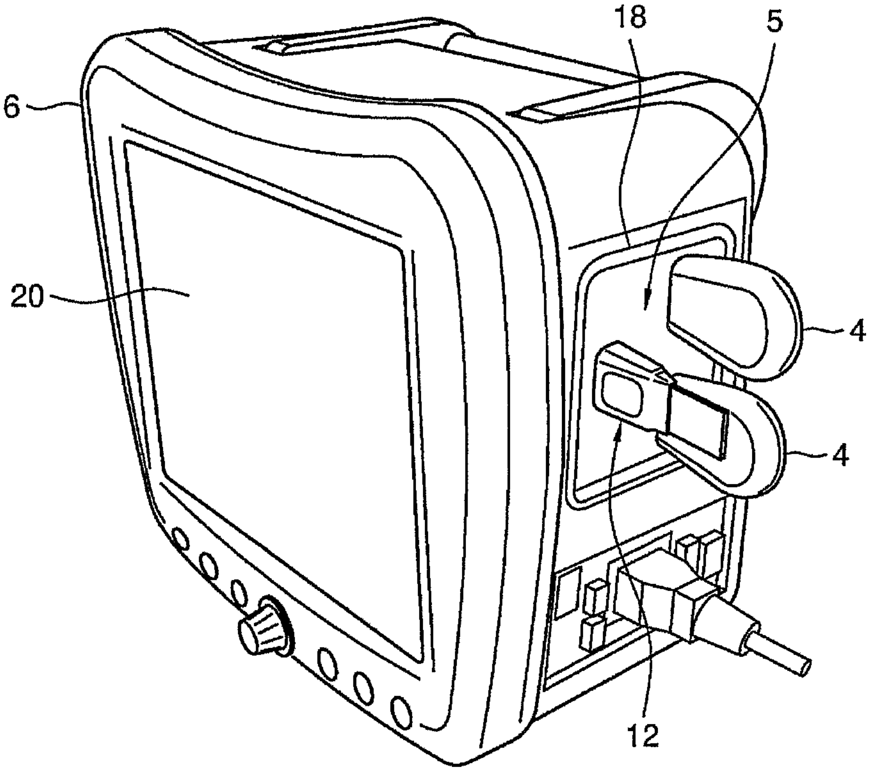
FIG. 7 illustrates a monitor unit in accordance with an embodiment of the present invention.

A monitor unit 6 that may be used in a system 1 in accordance with an embodiment, is illustrated in FIG. 7. The monitor comprises a display screen 20, and on the side of the monitor, the receiver unit 5 residing in a cradle (fourth connector) 18 can be seen. The first connector 12 inserted in the receiver unit 5, and two charging sensor units 4 can be seen in the figure. The invention is not limited to the monitor 6 shown, and neither to the use of the cradle 18. A standard monitor for presenting vital sign signals may likewise be applied in accordance with some embodiments, in which case the receiver unit 5 may be a separate unit with a standard connector for exchanging data signals with such a monitor.

Figure 8:
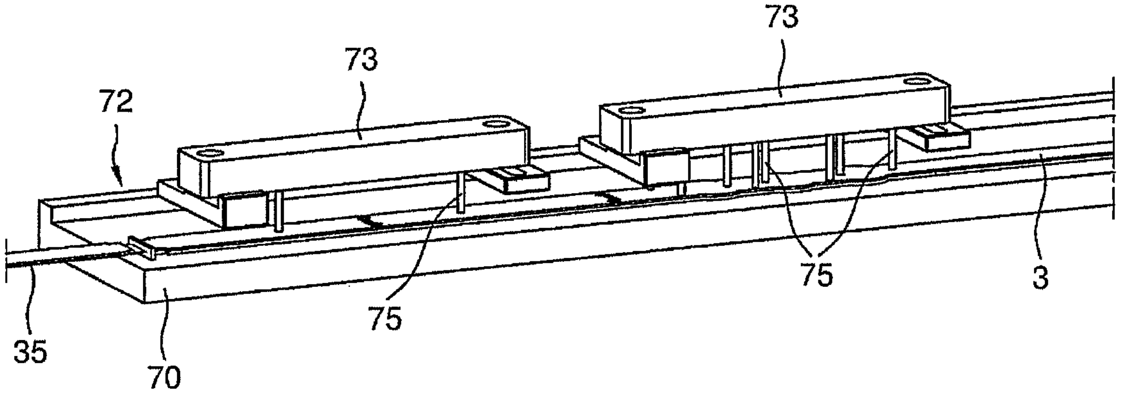
FIG. 8 Illustrates the multiple parts used in a manufacturing method in accordance with an embodiment of the present invention.
Figure 9:
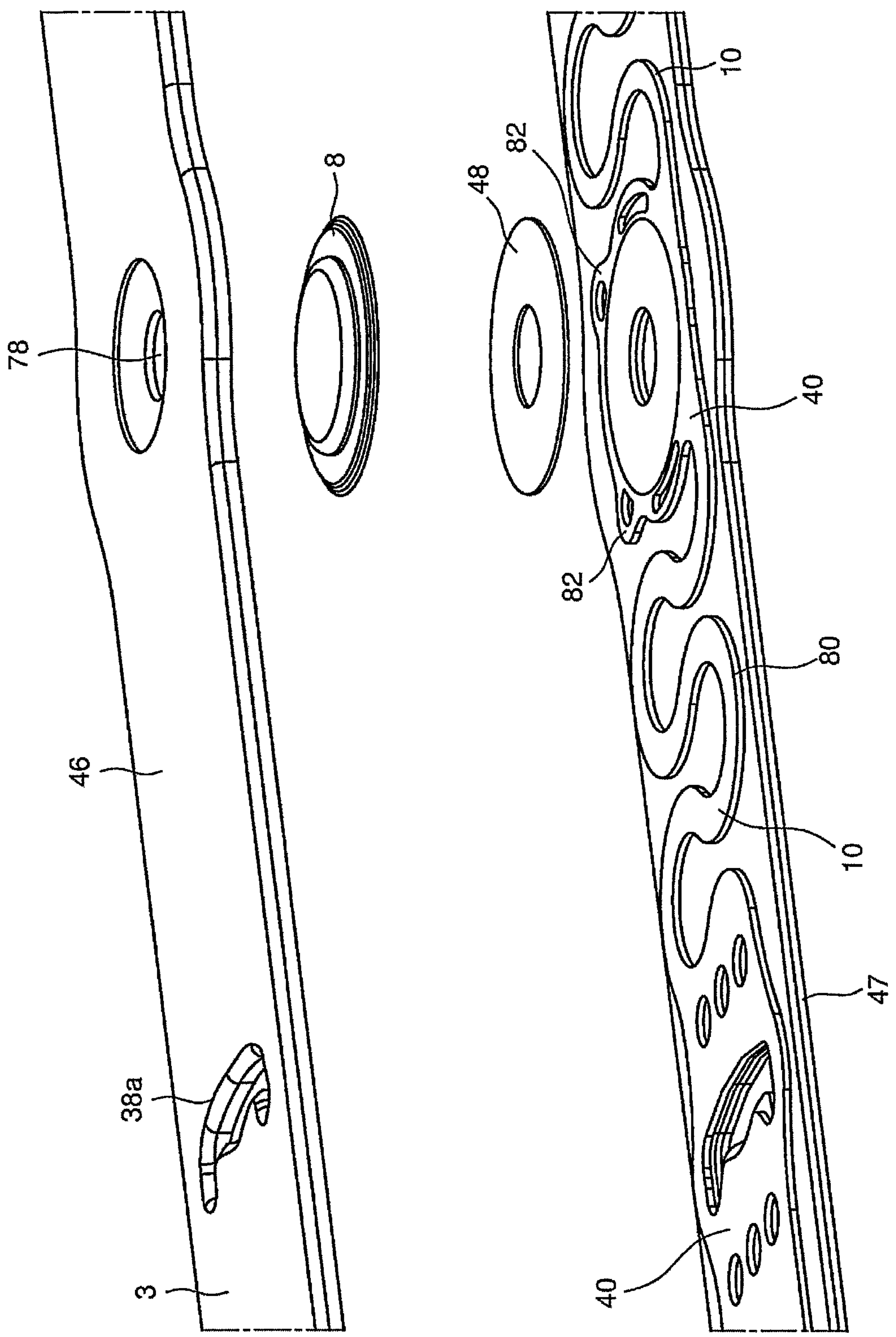
FIG. 9 shows in exploded view of a section of the wearable device in accordance with an embodiment of the invention.
Figure 10:
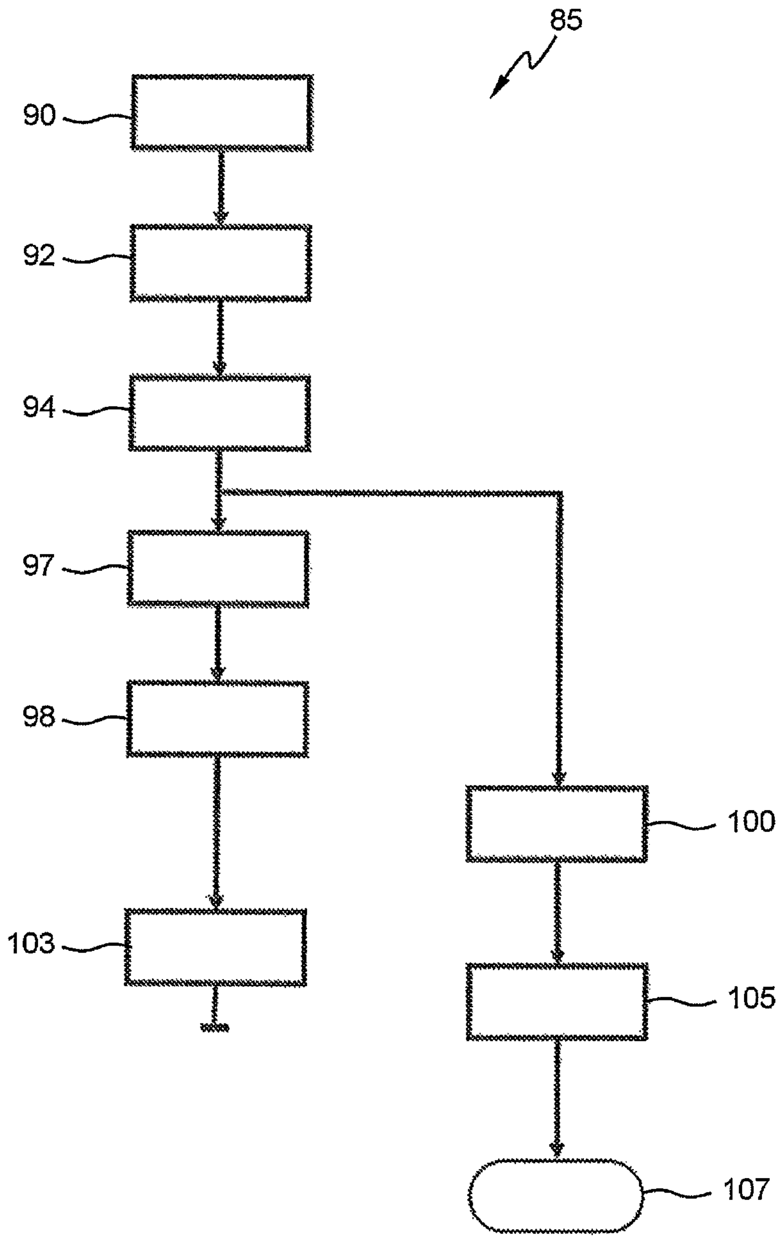
FIG. 10 illustrates a manufacturing method in accordance with an embodiment of the present invention.

FIGS. 8, 9 and 10 illustrate a manufacturing method in accordance with an embodiment of the invention, for manufacturing a flexible sensor belt 3 suitable for being worn around an abdominal part of a human body 2, in particular a baby 2. The belt to be manufactured preferably may be made of a liquid silicone rubber, although a thermoplastic elastomer or latex may likewise be used. A disadvantageous property of liquid silicone rubber is that it hardly binds with other materials, such as the electrodes 8 or the circuitry 40 of the belt 3. Therefore, specific measures need to be taken in order to prevent the layers 46 and 47 of the belt 3 to release prematurely, e.g. by a shear or a peel force in use, or already during manufacturing itself.

FIG. 8 illustrates the support layer 46 of the belt 3 residing in a first mould part 70. The circuit 35 of the first connector 12 to be formed, extends outside the mould part 70 at its end. A second mould part 72 is placed over the first mould part 70 in order to enable casting the longitudinal belt section 47 onto the support layer 46. The second mould part 72 contains holes through which a plurality of retaining elements 75 may be extended, which will hold the electrodes 8 and the circuitry 40 in place during casting of the longitudinal belt section 47.

FIG. 9 illustrates an enlarged part of an exploded view of the belt 3. During manufacturing, the support layer 46 including the holes 78 for receiving the electrodes 8 may be casted first, using a first mould part 70. Then, the electrodes 8 are applied to the support layer 46. This is done is such a way that the electrodes 8 protrude through the holes 78, as this enables the electrodes 8 to be in contact with the skin of the baby 2 in use. Thereafter, the electric circuitry 40 with the conductive paths 10 will need to be connected to the electrodes. The circuitry 40 may be fabricated separately, e.g. by etching, printing, or any other suitable technique known and available to the skilled person. The connection between the circuitry 40 and the electrodes 8 may be provided by an adhesive layer 48, as described above. This yields the electrodes 8 and the circuitry 40 to be mounted on the support layer 46, however not that proper bonding will be absent in case liquid silicone rubber was used to fabricate the support layer 46. The electrodes 8 are held in place only by friction between the electrodes 8 and the periphery of the holes 78. To properly fix all parts, i.e. the electrodes 8 and circuitry 40, the longitudinal belt section 47 needs to be casted onto the support layer 46. Liquid silicone rubber does bind properly to the liquid silicone rubber of the support layer, so once the casting is complete the elements will be properly fixed by being fully embedded and surrounded by the liquid silicone rubber. To enable casting while preventing the loose elements, i.e. the electrodes 8 and the circuitry 40, from displacing, use is made of the retaining elements 75. The retaining elements 75 for example hold the electrodes in place in locations 82. Furthermore, the meandering conductive path 10 may curl or otherwise deform during casting of layer 47. Therefore, a retaining element 75 may also be placed at location 80 during casting. Once the liquid flexible material has been injected under high pressure into the second mould part 72, the retaining elements 75 may be removed while the flexible material is still liquid and is able to flow. This will fill up the spaces left behind by the retaining elements 75. Alternatively, if it is desired to make direct connection with the circuitry 40 or the electrodes 8 later in use, it is also possible to first let the flexible material cure and then remove the retaining elements. There are various possibilities to implement this.

FIG. 10 schematically shows the method steps of the manufacturing method 85. The method 85 starts in step 90 by casting the support layer 46 using the first mould part. The support layer 46 is casted including the holes 78 for the electrodes. Then in step 92, one or more electrodes 8 are mounted by protruding these through the holes 78 as illustrated in FIGS. 4D and 9. In step 94, the flexible electronic circuit 40 is applied onto the electrodes 8, which may be achieved by using an adhesive layer 48 (e.g. glue or a different adhesive). Then, prior to casting in step 100, in step 97, retaining elements 75 will be extended into the second mould part 72 to retain the electrodes 8, and in step 98 retaining elements 75 are also extended such as to hold one or more conductive paths 10 of the circuitry 40. The steps 97, 98, and 103 in method 85 are drawn as a separate branch, because the retaining steps will continue to be performed until the casting is completed and these steps are thus ran in parallel to steps 100 and 105. Next after starting steps 97 and 98, in step 100 the casting of the flexible material will be performed by casting e.g. liquid silicone rubber into the second mould part 72 under pressure. The electrodes 8 and circuitry 40 are retained during the casting and will not move. After completion of step 100, either before or during the curing step 105 of the liquid silicone rubber, the retaining elements may be retracted in step 103 to enable the flow of casted material to fill up the spaces left behind by the retaining elements 75. After step 103, this branch of the method will end. The method itself will continue unit the curing step 105 has been completed and the manufactured belt 3 has been released from the mould.

Various Implementations of the System

Below, some variants and suggestions are described relating to the system described above. The system has been designed to provide a flexible solution that is sufficiently robust and can be easily and securely applied in a hospital where multiple babies may have to be monitored continuously over a longer period of time.

To this end, there is provided a system for monitoring one or more vital signs of a human body, in particular a baby, the system including a wearable device comprising a carrier suitable for being worn around an abdominal part of the body, and an electrode arrangement comprising a plurality of conductive electrodes, wherein the electrodes are arranged on the carrier such as to be brought in contact with a skin of the body in use, and wherein the electrodes are arranged for receiving electric physiological signals from the body for enabling said monitoring of the one or more vital signs, wherein the system further includes a sensor unit configured for receiving the electric physiological signals from the electrodes and for providing a sensor signal based on the received electric physiological signals; wherein system comprises a connector assembly comprising a first connector and a second connector, the first and the second connector being complementary such as to enable establishing a connection between the first and the second connector, wherein first connector is comprised by the wearable device, and wherein the wearable device comprises one or more conductive paths between the electrode arrangement and the first connector for electrically connecting the electrode arrangement with the connector; and wherein the second connector is comprised by the sensor unit for enabling to establish a detachable connection between the sensor unit and the wearable device for receiving the electric physiological signals.

The system of the present invention applies a connector assembly to enable disconnecting the sensor unit from the wearable device. As a result, the wearable device can be easily replaced without having to replace the sensor unit. Furthermore, the sensor unit can be easily disconnected in order to perform charging or maintenance, independent from the replacement period of the disposable wearable device. For example, suppose the wearable device needs to be replaced once every three days, and the sensor unit needs to be charged once every two days, the charging can be performed without having to replace the disposable wearable device, and the disposable wearable device can be replaced without having to exchange the sensor unit at half charge. Periodic replacement of the disposable wearable device is needed to prevent buildup of filth and pathogens on the wearable device worn by the baby. The possibility to exchange the wearable device and sensor units each within their own maintenance cycle, provides a flexible and low-cost solution that allows to provide a disposable wearable device in combination with good quality or even the high end sensor units. A disposable belt or wearable device can thus be achieved without trade-off with respect to the use of good quality electronic components and functionality implemented therein.

In accordance with some embodiments, the system further comprises a receiver unit configured for receiving the sensor signal from the sensor unit, the receiver unit being configured for providing a vital signs signal to a monitor for presentation of the vital signs signal on a display. The use of a separate receiver unit provides additional flexibility to the system of the invention in order to enable the use thereof with any arbitrary type of monitoring equipment. The receiver unit may be a separate unit, or may have been integrated in a monitoring unit. Furthermore, as a separate unit, communication between the receiver unit and the monitor may be by means of a wireline signal or a wireless signal without departing from the claimed invention. The used of a wireline signal, via a cable or a connector to the monitor, has the benefit of being more secure in terms of data protection and more reliable because the risk of picking up a different signal accidentally is prevented. The benefits of a wireless signal is provided by the absence of a cable and the increased range at which a receiver unit may be remote from the monitor. However, these latter benefits of the wireless signal may be diminished if other components of the system will be enabled to communicate wirelessly, as in the embodiments below.

In some embodiments, the sensor unit is configured for establishing a wireless connection with the receiver unit for providing the sensor signal to the receiver unit as a wireless signal. The application of a wireless signal between the sensor unit and the receiver unit is beneficial over the application of a wireless signal between the receiver unit and the monitor. In order to enable the wearable device to be as low cost as possible, the electronics are preferably implemented on the sensor unit rather than the carrier or any other part of the wearable device. Preferably, the carrier comprises the electrodes and the conductive paths to the first connector. In a preferred embodiment, the sensor unit is therefore connected to the wearable device via the connector and therefore resides close to the baby. Therefore, there are benefits in wirelessly communicating the sensor signal to the receiver unit, enabling the sensor unit to be remote from that receiver unit which resides at the monitor.

In some embodiments, the sensor unit is configured for providing the wireless signal including an identification key data for enabling identification of the sensor unit providing the sensor signal after receipt thereof by the receiver unit. The application of identification key data in order to uniquely identify the sensor signal after received thereof, provides the advantage of enabling secure communication with the receiver unit. Furthermore, once the receiver unit and monitor our parents with the sensor unit, do use of the identification key data in the center signal prevents the inadvertent mixing up of sensor signals from different sensor units connected to different wearable devices.

In some embodiments, the receiver unit comprises a processor for processing the sensor signal such as to provide the vital signs signal based on the received sensor signal. The processor may be applied for adding additional intelligence to the receiver unit. For example, the receiver unit may comprise the algorithms for analyzing the sensor signals and providing the vital sign signals to the monitor. Furthermore, in accordance with just a further embodiment, the processor is configured for establishing the identification key data based on a unique identification key, and wherein the receiver unit is configured for providing the identification key data to the sensor unit prior to receiving the wireless signal. In these embodiment, the processor of the receiver unit is able to generate a unique identification key that can be used for establishing the identification key data to be provided to the center unit, for example. Communication to the sensor unit may take place in various different ways, however in some embodiments a pairing method is applied in order to associate the receiver unit with the sensor unit.

In certain embodiments, in addition to the sensor unit, the receiver unit comprises a further second connector complementary to the first connector for enabling to establish a detachable connection between the receiver unit and the wearable device. In these embodiments, the receiver unit can be connected to the wearable device via the same first connector of the wearable device. This enables direct communication between the receiver unit and the wearable device, such as for example in order to perform in initialization or pairing method.

In some embodiments, the receiver unit is configured for communicating the identification data to the wearable device during a pairing method via a wireline connection through the first and further second connector, and wherein the wearable device is configured for storing the identification key data in a memory comprised by the wearable device. For example, if in these embodiments that receiver unit is connected to the wearable device via the connector assembly, the identification key data can be stored in the memory of the wearable device. Thereafter, the receiver unit may be disconnected from the wearable device, and the sensor unit may be connected to the wearable device for the connector assembly. The sensor unit may then obtain the identification key data directly from the memory on the wearable device. This provides a secure way of exchanging the identification key data between the receiver unit and the sensor unit.

In further embodiments, the sensor unit is configured for receiving the identification key data through the connector assembly via an established connection between the sensor unit and the wearable device, for using the received identification key data with the wireless signal. These embodiments have been briefly discussed above, and enable the sensor unit to obtain the identification key data from the memory of the wearable device.

In some embodiment, the receiver unit is an integral part of the monitor. For example, the receiver unit may be integrated on chip on a controller of the monitor, or may be an implemented module or unit within the housing of the monitor. In other embodiments, the receiver unit may comprise a third connector, the third connector being configured for cooperating with a fourth connector comprised by the monitor to establish an electrical connection between the receiver unit and the monitor. In these embodiments, the connector may be a standard type connector for data communication with a peripheral device, already present on most monitors. However, the monitor may also include a dedicated connector for connecting a receiver unit of the system, the latter allowing the supplier of the system to selectively implement compatibility on certain types of monitors that fulfill specific technical requirements required for monitoring pre-term babies. Yet, in other embodiments, the receiver unit is configured for establishing a further wireless connection with the monitor for providing the vital signs signal via a further wireless signal. This may be beneficial in some implementations, for example where power supply to the sensor unit may be implemented passively (e.g. passive RFID or remote charging by electromagnetic waves) and the receiver unit is typically located close to the sensor unit to provide the charging functionality. The above embodiments have already been briefly touched upon above, and enable the receiver unit to be part of the monitor, or to be separate therefrom, and perform communication with the monitor in different ways.

In some embodiments, the sensor unit is configured for performing wireless data communication via at least one of: Bluetooth, such as Bluetooth low energy; Radio Frequency Identification; Zigbee; or Wi-fi. The skilled person may appreciate that the above wireless communication protocols are not the only protocols that may be implemented by the sensor unit and receiver unit to exchange sensor signals and/or data. however these data protocols maybe applied indoor and over short distances, and some of them such as Bluetooth low energy or RFID, maybe performs in low energy instruments such as some embodiments of the system of the present invention.

In some embodiments, the receiver unit, for cooperating with the second connector of the sensor unit, further comprises at least one of: one or more fifth connectors, or one or more first connectors. This allows the receiver unit to be connected to the sensor units directly, or to a further peripheral device. In particular, in some embodiments, the sensor unit comprises a battery, and wherein the at least one of the one or more fifth connectors or the one or more first connectors comprised by the receiver unit are configured for powering the battery of the sensor unit. With use of the one or more fifth connectors or the one or more the first connectors as described above, the sensor units can easily be charged via the receiver unit. For example the sensor units can be connected to the first or fifth connectors of the receiver units, which may comprise a power supply line in order to charge the battery of the sensor units. Multiple of these connectors may be present on the receiver unit.

In accordance with a second aspect of the invention, there is provided a wearable device for use in a system according to the first aspect, wherein the wearable device comprises a carrier suitable for being worn around an abdominal part of the body, and an electrode arrangement comprising a plurality of conductive electrodes, wherein the electrodes are arranged on the carrier such as to be brought in contact with a skin of the body in use, and wherein the electrodes are arranged for receiving electric physiological signals from the body for enabling said monitoring of the one or more vital signs; wherein the wearable device further comprises a first connector, the first connector being configured for cooperating with a second connector or a further second connector for forming a connector assembly for establishing a detachable connection through which electrical signals can be exchanged between the wearable device and a further unit; and wherein the wearable device comprises one or more conductive paths between the electrode arrangement and the first connector for bearing the electric physiological signals.

Yet in accordance with a second aspect of the invention, there is provided a sensor unit for use in a system according to the first aspect, or configured for cooperating with a wearable device according to the second aspect, the sensor unit being configured for receiving electric physiological signals from one or more electrodes of the wearable device, and for providing a sensor signal based on the received electric physiological signals; wherein the sensor unit further comprises a second connector being complementary to a first connector of the wearable device such as to cooperate therewith for forming a connector assembly, for enabling to establish a detachable connection between the sensor unit and the wearable device for receiving the electric physiological signals.

In some embodiments, as explained above, the sensor unit may be configured for establishing a wireless connection with a receiver unit for providing the sensor signal to the receiver unit as a wireless signal. Furthermore, in some embodiments, the sensor unit is configured for obtaining identification key data stored in a memory of the wearable device, and for providing the wireless signal including the identification key data, for enabling identification of the sensor unit after receipt of the sensor signal by a receiver unit.

Yet in accordance with a fourth aspect of the invention, there is provided a receiver unit for use in a system according to the first aspect, or configured for cooperating with a wearable device according to the second aspect, or configured for cooperating with a sensor unit according to the third aspect, wherein the receiver unit comprises a communication unit for receiving the sensor signal from the sensor unit, the receiver unit being configured for providing a vital signs signal to a monitor for presentation of the vital signs signal on a display. The receiver unit, in some embodiments, comprises a processor, wherein the processor is configured for establishing identification key data based on a unique identification key, and wherein the receiver unit is configured for providing the identification key data to the sensor unit prior to receiving a wireless signal from the sensor unit. Furthermore, the receiver unit may in some embodiments comprise a second connector complementary to a first connector comprised by the wearable unit, the first and the second connecter together forming a connector assembly, for enabling to establish a detachable connection between the receiver unit and the wearable device; wherein the receiver unit is configured for communicating the identification data to the wearable device during a pairing method via a wireline connection through the connector assembly, and wherein the wearable device is configured for storing the identification key data in a memory comprised by the wearable device.

Yet in accordance with a fifth aspect of the invention, there is provided a method of pairing a sensor unit and a receiver unit in a system according to the first aspect, wherein the receiver unit comprises a processor, wherein the processor is configured for establishing identification key data based on a unique identification key, and wherein the sensor unit is configured for establishing a wireless connection with the receiver unit for providing the sensor signal to the receiver unit as a wireless signal, and wherein the sensor unit is configured for providing the wireless signal including an identification key data, the method comprising: transmitting, via a wireline connection between the receiver unit and a wearable device, the identification key data to the wearable device and storing the identification key data in a memory of the wearable device; disconnecting the receiver unit from the wearable device; establishing a wireline connection between a sensor unit and the wearable device; and obtaining, by the sensor unit, the identification key data from the memory. An advantage of the method in accordance with this fifth aspect of the invention, is that by connecting the receiver unit to the wearable device, a secure wireline connection is obtained that enables to securely transmit the identification key data to the disposable wearable device. Once stored therein in a memory of the wearable, any sensor unit can be connected to the wearable device in order to obtain the identification key data from the memory and start transmitting securely to the paired receiver unit. Multiple sensor units may thus be used in order to charge one or more sensor units, while using another one with the wearable device.

The present invention has been described in terms of some specific embodiments thereof. It will be appreciated that the embodiments shown in the drawings and described herein are intended for illustrated purposes only and are not by any manner or means intended to be restrictive on the invention. It is believed that the operation and construction of the present invention will be apparent from the foregoing description and drawings appended thereto. It will be clear to the skilled person that the invention is not limited to any embodiment herein described and that modifications are possible which should be considered within the scope of the appended claims. Also kinematic inversions are considered inherently disclosed and to be within the scope of the invention. Moreover, any of the components and elements of the various embodiments disclosed may be combined or may be incorporated in other embodiments where considered necessary, desired or preferred, without departing from the scope of the invention as defined in the claims.

In the claims, any reference signs shall not be construed as limiting the claim. The term ‘comprising’ and ‘including’ when used in this description or the appended claims should not be construed in an exclusive or exhaustive sense but rather in an inclusive sense. Thus the expression ‘comprising’ as used herein does not exclude the presence of other elements or steps in addition to those listed in any claim. Furthermore, the words ‘a’ and ‘an’ shall not be construed as limited to ‘only one’, but instead are used to mean ‘at least one’, and do not exclude a plurality. Features that are not specifically or explicitly described or claimed may be additionally included in the structure of the invention within its scope. Expressions such as: “means for . . . ” should be read as: “component configured for . . . ” or “member constructed to . . . ” and should be construed to include equivalents for the structures disclosed. The use of expressions like: “critical”, “preferred”, “especially preferred” etc. is not intended to limit the invention. Additions, deletions, and modifications within the purview of the skilled person may generally be made without departing from the spirit and scope of the invention, as is determined by the claims. The invention may be practiced otherwise then as specifically described herein, and is only limited by the appended claims.

The invention claimed is:

1. A method of manufacturing a flexible sensor belt suitable for being worn around an abdominal part of a human body, the method comprising the steps of:

applying, one or more electrodes in a mould; and casting, using a mould, a belt containing the electrodes by injecting a flexible material under pressure, such as to immerse the electrodes in the belt, and such that a contact area of the electrodes protrudes from the belt;

wherein, for performing the step of casting, the mould is configured to allow one or more retaining elements to extend into an internal space of the mould; and wherein the step of casting the belt comprises a step of retaining the one or more electrodes using the one or more retaining elements extending into the mould, for holding the electrodes in place during casting.

2. The method according to claim 1, the method comprising the steps of:

providing a support layer made of the flexible material;

applying, onto the support layer, the one or more electrodes; and casting, a complementary layer onto the support layer using the flexible material, such as to cover the one or more electrodes with the complementary layer formed on the support layer to thereby immerse the electrodes in the flexible material.

3. The method according to claim 2, wherein the support layer is provided by casting, using a first mould part, the support layer using the flexible material, such that the support layer comprises one or more holes;

wherein the step of applying the electrodes comprises:

applying, onto the support layer, the one or more electrodes, such that the one or more electrodes protrude the one or more holes, and wherein the electrodes are made of an electrically conductive material;

wherein the step of casting the complementary layer comprises:

casting, using a second mould part complementary to the first mould part, a longitudinal belt section onto the support layer using the flexible material, such as to cover the one or more electrodes with the longitudinal belt section formed on the support layer to thereby immerse the electrodes in the flexible material;

wherein the step of casting the longitudinal belt section comprises a step of retaining the one or more electrodes using the one or more retaining elements.

4. The method according to claim 3, further comprising a step of setting of the longitudinal belt section after casting thereof, wherein during said setting the method comprises retracting of the one or more retaining elements.

5. The method according to claim 3, wherein the flexible material comprises at least one of: a liquid silicone rubber, a thermoplastic elastomer, latex, thermoset rubber.

6. The method according to claim 1, wherein the step of applying the one or more electrodes comprises:

applying a flexible electronic circuit such as to electrically connect the one or one or electrodes.

7. The method according claim 6, wherein at least one of:

the flexible electronic circuit is attached to the one or more electrodes after applying the electrodes onto the support layer;

the electronic circuit is attached to the one or more electrodes, and the electronic circuit including the electrodes is applied onto the support layer;

the electronic circuit and the one or more electrodes are integrally formed, and the integrally formed circuit is applied to the support layer.

8. The method according to claim 6, wherein the flexible electronic circuit comprises one or more conductive paths, the one or more conductive paths being shaped such as to form at least one of: a wavy path; a zigzag path; or a meandering path; and wherein the method comprises, during said casting of the belt section, a step of retaining the one or more conductive paths using one or more retaining elements.

9. The method according to claim 4, wherein the flexible material comprises at least one of: a liquid silicone rubber, a thermoplastic elastomer, latex, thermoset rubber.

10. The method according to claim 7, wherein the flexible electronic circuit comprises one or more conductive paths, the one or more conductive paths being shaped such as to form at least one of: a wavy path; a zigzag path; or a meandering path; and wherein the method comprises, during said casting of the belt section, a step of retaining the one or more conductive paths using one or more retaining elements.

* * * * *